United States Patent
Saft et al.

(10) Patent No.: US 8,193,383 B2
(45) Date of Patent: Jun. 5, 2012

(54) PROCESS FOR CONTINUOUSLY PREPARING FATTY ACID METHYL ESTERS OR FATTY ESTERS

(75) Inventors: Helmut Saft, Niddatal (DE); Klaus Hohmann, Hofheim (DE); Rudolph Bönsch, Nackenheim (DE)

(73) Assignee: Lurgi GmbH, Frankfurt am Main (DE)

( * ) Notice: Subject to any disclaimer, the term of this patent is extended or adjusted under 35 U.S.C. 154(b) by 453 days.

(21) Appl. No.: 12/441,088

(22) PCT Filed: Jul. 31, 2007

(86) PCT No.: PCT/EP2007/006745
§ 371 (c)(1),
(2), (4) Date: Nov. 30, 2009

(87) PCT Pub. No.: WO2008/034485
PCT Pub. Date: Mar. 27, 2008

(65) Prior Publication Data
US 2010/0105935 A1    Apr. 29, 2010

(30) Foreign Application Priority Data
Sep. 21, 2006 (DE) .......................... 10 2006 044 467

(51) Int. Cl.
*C11C 3/00* (2006.01)
(52) U.S. Cl. .................................................... 554/167
(58) Field of Classification Search .................... 554/167
See application file for complete search history.

(56) References Cited

FOREIGN PATENT DOCUMENTS

| EP | 523767 | * | 1/1993 |
|----|--------|---|--------|
| EP | 0523767 A | | 1/1993 |
| WO | 2006/088254 A | | 8/2006 |

OTHER PUBLICATIONS

English Language Abstract for EP 0523767.

* cited by examiner

*Primary Examiner* — Deborah D Carr
(74) *Attorney, Agent, or Firm* — Norris McLaughlin & Marcus PA

(57) ABSTRACT

In a process for producing fatty acid methyl ester (FAME) from fats or oils by transesterification with methanol in the presence of an alkaline catalyst in at least two reaction stages traversed in succession, each consisting of a stirred-tank reactor and a downstream separator, a phase containing FAME and a phase containing glycerol are generated, which are separated in the separator, wherein the phase containing FAME is recirculated into the stirred-tank reactor of the next succeeding reaction stage and the phase containing glycerol is recirculated into the stirred-tank reactor of the first reaction stage, and the crude FAME withdrawn from the separator of the last reaction stage is transferred into a separator and the FAME withdrawn is dried. To increase the yield of FAME, the aqueous phase containing glycerol, methanol, undissociated soaps and FAME, which is obtained upon withdrawal of the FAME, is thoroughly mixed with the phases withdrawn from the separators of the first to penultimate reaction stages, which contain glycerol and FAME, and the mixture is separated in a separator into a phase containing FAME and a phase containing glycerol.

5 Claims, 1 Drawing Sheet

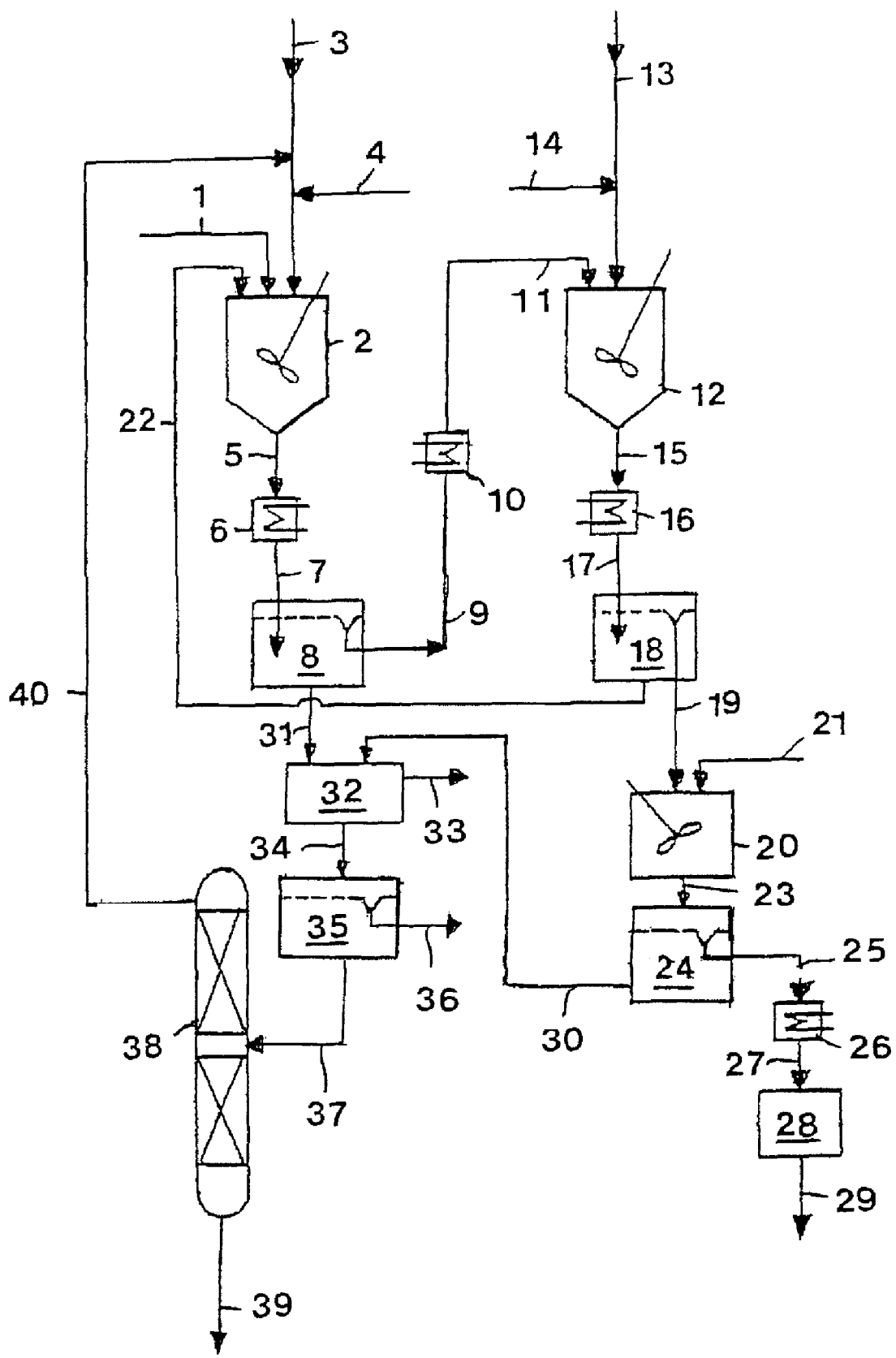

PROCESS FOR CONTINUOUSLY PREPARING FATTY ACID METHYL ESTERS OR FATTY ESTERS

This application is a 371 application of PCT/EP2007/006745 filed Jul. 31, 2007, which claims priority to the German application DE 10 2006 044 467.1 filed Sep. 21, 2006.

This invention relates to a process for the continuous production of fatty acid methyl ester (FAME) or fatty acid ethyl ester (FAEE), in particular for Diesel combustion engines, from vegetable and/or animal fats and/or oils by transesterification of the triglycerides contained in the fats and oils with methanol or ethanol in the presence of an alkaline catalyst in liquid phase at a temperature of 30 to 90° C. and at atmospheric pressure in at least two reaction stages traversed in succession, which each consist of a stirred-tank reactor with downstream separator, in that a light phase containing FAME or FAEE and a heavy phase containing glycerol are generated in the stirred-tank reactors, the light phase containing FAME or FAEE and the heavy phase containing glycerol are separated from each other in the separator downstream of the respective stirred-tank reactor, the phase containing FAME or FAEE is supplied to the stirred-tank reactor of the next succeeding reaction stage, the glycerol-containing phase withdrawn from the separator of the second to last reaction stages is recirculated into the stirred-tank reactor of the first reaction stage, the crude FAME or crude FAEE withdrawn from the separator of the last reaction stage is transferred into a separator after acid water washing, and the FAME or FAEE withdrawn from this separator is dried.

The above-described process known from DE-A-4123928 for generating fatty acid methyl ester (FAME) or fatty acid ethyl ester (FAEE) and glycerol by transesterification of oils or fats is operated in at least two reaction stages, wherein each reaction stage includes a mixing reactor with a downstream separator for physical separation into a light phase rich in ester and a heavy phase rich in glycerol. To the mixing reactor of the first reaction stage, oil or fat as well as methanol or ethanol and catalyst is supplied, and to the mixing reactor of the second and each further reaction stage, methanol or ethanol and catalyst is supplied together with the light phase rich in ester, which is obtained in the respectively preceding reaction stage. The heavy phase rich in glycerol, which is separated in the separator of the second to last reaction stages, is at least partly recirculated into the mixing reactor of the first reaction stage. From the light phase rich in ester, which is separated in the last reaction stage, FAME or FAEE is obtained by at least one further separation treatment. This process, with which relatively large throughputs of material can be achieved, can be performed in a relatively simple and inexpensive way.

The total amount of methanol or ethanol supplied to the mixing reactors is 1 to 3 times the stoichiometrically necessary quantity. NaOH, KOH, CH$_3$ONa or C$_2$H$_5$ONa preferably are used as alkaline catalysts, generally in a concentration of 0.1 to 1.0 wt-%, based on the amount of fat or oil to be converted.

In operation of the process, 20 to 60%, preferably 35 to 45%, of the entire methanol or ethanol and 20 to 60%, preferably 30 to 50%, of the entire alkaline catalyst expediently are supplied to the mixing reactor of the first reaction stage. The rest of the methanol or ethanol and of the catalyst is charged to the mixing reactor of the second reaction stage. What is disregarded here are the small amounts which by recirculation of the phase rich in glycerol from the separator of the second reaction stage get into the mixing reactor of the first reaction stage.

From the heavy phase rich in glycerol, which is withdrawn from the separator of the first reaction stage, the methanol or ethanol is thermally separated from the glycerol and recirculated into the mixing reactor of the first reaction stage. Upon extraction with water, the light phase rich in ester, which is discharged from the separator of the last reaction stage, is subjected to a separation under the influence of centrifugal force and separated into FAME or FAEE with a water content of not more than 2.0 wt-% and into an aqueous phase containing methanol or ethanol and glycerol. To reduce the water content of FAME or FAEE, it is possible to heat the FAME or FAEE in a heat exchanger and subsequently perform drying. The aqueous phase containing methanol or ethanol and glycerol, which is almost free from methanol or ethanol, is added to the heavy phase rich in glycerol, which is discharged from the separator of the first reaction stage, prior to the thermal separation thereof.

In the two-phase separation of the transesterification products in the separators downstream of the mixing reactors into a light phase rich in ester and a heavy phase rich in glycerol, up to 3 wt-% of ester are left in the heavy phase rich in glycerol. In addition, up to 2 wt-% of ester are washed out in the acid water washing of the phase rich in ester recovered from the last reaction stage, which upon separation of the FAME or FAEE are contained in the aqueous phase containing methanol or ethanol, glycerol and undissociated soaps. In the thermal separation of the mixture consisting of the phase rich in glycerol of the first reaction stage and of methanol or ethanol and glycerol of the aqueous phase into methanol or ethanol on the one hand and crude glycerol on the other hand, some ester remains in the crude glycerol.

It is the object of the present invention to develop the process described above such that the total yield of FAME or FAEE is increased and hence the economy of the process recognizably is improved.

This object is solved in that the aqueous phase containing 0.5 to 2 wt-% of glycerol, 2 to 8 wt-% of methanol or ethanol, 0.05 to 0.5 wt-% of undissociated soaps and 0.05 to 0.5 wt-% of FAME or FAEE, which is obtained upon separation of FAME or FAEE after the acid water washing, is thoroughly mixed with the heavy phases withdrawn from the separators of the first to penultimate reaction stages, which contain glycerol and 0.5 to 3 wt-% of FAME or FAEE, and then is supplied to a separator, in which a separation into a phase containing FAME or FAEE and a phase containing glycerol is performed.

A development of this measure consists in that the phase containing glycerol is thermally separated into crude glycerol and methanol or ethanol, and methanol or ethanol and the FAME or FAEE withdrawn from the separator are recirculated into the stirred-tank reactor of the first reaction stage.

One aspect of the invention consists in that the aqueous phase containing 0.5 to 2 wt-% of glycerol, 2 to 8 wt-% of methanol or ethanol, 0.05 to 0.5 wt-% of undissociated soaps and 0.05 to 0.5 wt-% of FAME or FAEE is thoroughly mixed with the heavy phases containing glycerol and 0.5 to 3 wt-% of FAME or FAEE at a pH value of 0.5 to <6, preferably a pH value of 1 to 4, and at a temperature of 40 to 60° C., preferably a temperature of 40 to 50° C., for a period of 15 to 60 min, preferably for a period of 20 to 45 min, and the mixture is cooled to a temperature of 25 to 35° C., so that the FAME or FAEE will float on the mixture and can easily be withdrawn.

Expediently, the acid water washing of the crude FAME or crude FAEE is performed with a weak acid, preferably with 1 to 5% hydrochloric acid, sulfuric acid, phosphoric acid or citric acid in an intensive mixer.

The invention will be explained in detail below by means of an embodiment and with reference to a process flow diagram shown in the drawing.

1000 kg/h of rape-seed oil pretreated by desliming, bleaching and deacidifying are supplied to the stirred-tank reaktor (2) of the first reaction stage via conduit (1), 74 kg/h of anhydrous methanol are supplied via conduit (3), and 2.4 kg/h of sodium methylate ($CH_3ONa$) serving as catalyst are supplied via conduit (4). In the production of FAEE, sodium ethylate ($C_2H_5ONa$) is used as catalyst. These components are intensively mixed in the stirred-tank reactor (2) at a temperature of 75° C. and at atmospheric pressure. As is known, the stirred-tank reactor (2) can consist of a plurality of mixing chambers arranged in series. The rape-seed oil substantially consists of glycerol as basic carrier with three long fatty acid chains ($C_{18}$ chains) attached thereto; in the transesterification, the same react with methanol, with the catalyst promoting the reaction. In the transesterification, the long-chain branched molecule is exchanged for three individual, shorter molecules. Oils and fats consist of 97% glycerol as basic carrier and fatty acid chains attached thereto with 16 to 22 C atoms, which have linked to the glycerol by releasing water; such compounds are referred to as triglycerides. The rest are free fatty acids, vitamins, water, phosphorus compounds and small amounts of sulfur. From the stirred-tank reactor (2), the transesterification product flows through conduit (5) over the heat exchanger (6), is cooled in the same to a temperature of 60° C., and is then charged via conduit (7) to the separator (8), in which a separation into a light phase containing FAME and a heavy phase containing glycerol is effected. The light phase containing FAME, which is withdrawn from the separator (8) via conduit (9), is passed over the heat exchanger (10), in which the temperature of the transesterification product is lowered to 45° C., and subsequently supplied via conduit (11) to the stirred-tank reactor (12) of the second reaction stage. Via conduit (13), 118 kg/h of methanol and via conduit (14) 3.6 kg/h of $CH_3ONa$ as catalyst are added to the transesterification product, and the components are intensively mixed at a temperature of 60° C. and at atmospheric pressure. The transesterification product flowing off from the stirred-tank reactor (12) via conduit (15) is cooled to a temperature of 35° C. in the succeeding heat exchanger (16) and then charged via conduit (17) to the separator (18), from which crude FAME, in which at least 99% of the fatty acids contained in the rape-seed oil are present in the form of FAME, is withdrawn and supplied to a mixer (20). In the mixer (20), the residual soaps contained in the crude FAME are dissociated by adding 3% hydrochloric acid flowing in via conduit (21) with a pH value of 6 to 7, and the catalyst as well as the phosphorus compounds are destroyed and the water-soluble substances, substantially methanol and glycerol, are extracted. The heavy phase containing glycerol, which is withdrawn from the separator (18) via conduit (22), is recirculated into the stirred-tank reactor (1) of the first reaction stage. The phase containing FAME, which flows off from the mixer (20) via conduit (23), is separated in a downstream separator (24) into FAME with a water content of less than 2 wt-% and into an aqueous phase substantially containing 1.5 wt-% of glycerol, 4.5 wt-% of methanol, 0.3 wt-% of undissociated soaps and 0.25 wt-% of FAME. Upon preheating to a temperature of 95° C. in the downstream heat exchanger (26), the FAME discharged from the separator (24) via conduit (25) is supplied via conduit (27) to a vacuum drier (28), in which the water contained in the FAME is removed. Via conduit (29), 1001 kg/h of FAME are discharged from the vacuum drier (28), which upon examination in accordance with indicated testing methods satisfies the requirements of the European standard for biodiesel (DIN EN 14214).

The aqueous phase of the aforementioned composition, which leaves the separator (24) via conduit (30), and the heavy phase containing glycerol and 2.5 wt-% of FAME, which flows off from the separator (8) of the first reaction stage via conduit (31), are introduced into the stirred tank stage (32), in which the same are intensively mixed for a period of 30 min, heated to a temperature of 24° C., and the pH value is adjusted to 2 by adding hydrochloric acid. The FAME floating on the surface of the mixture is discharged from the stirred tank (32) via conduit (33) and can be recirculated into the stirred tank (2) of the first reaction stage. The phase containing methanol and FAME beside glycerol is discharged from the stirred tank (32) via conduit (34) and charged to the separator (35), in which FAME is deposited almost completely at a temperature of 20° C. and with a concentration gradient of almost 7% in the phase containing glycerol, and 0.5 kg/h of FAME are withdrawn from the separator (35) via conduit (36). The remaining aqueous phase, which almost only contains glycerol and methanol, flows via conduit (37) to the rectification column (38), in which a separation into a glycerol phase and a methanol phase is effected at a bottom temperature of 110° C. and at atmospheric pressure. From the bottom of the rectification column (38), 1.5% glycerol is withdrawn via conduit (39), and at the top 99.9% methanol is withdrawn via conduit (40). The methanol is fed into the methanol stream flowing in conduit (3) and supplied to the stirred-tank reactor (2) of the first reaction stage, and the aqueous glycerol phase is supplied to a cleaning.

By means of the measures of the invention it is possible to increase the total yield of FAME and FAEE by up to 2% and thus distinctly improve the total economy of the process.

The invention claimed is:

1. A process for the continuous production of fatty acid methyl ester (FAME) or fatty acid ethyl ester (FAEE) from vegetable and/or animal fats and/or oils by transesterification of the triglycerides contained in the fats and oils with methanol or ethanol in the presence of an alkaline catalyst in liquid phase at a temperature of 30 to 90° C. and at atmospheric pressure in at least two reaction stages traversed in succession, which each comprise a stirred-tank reactor with downstream separator, in that a light phase containing FAME or FAEE and a heavy phase containing glycerol are generated in the stirred-tank reactors, the light phase containing FAME or FAEE and the heavy phase containing glycerol are separated from each other in the separator downstream of the respective stirred-tank reactor, the phase containing FAME or FAEE is supplied to the stirred-tank reactor of the next succeeding reaction stage, the glycerol-containing phase withdrawn from the separator of the second to last reaction stages is recirculated into the stirred-tank reactor of the first reaction stage, the crude FAME or crude FAEE withdrawn from the separator of the last reaction stage is transferred into a separator after acid water washing, and the FAME or FAEE withdrawn from this separator is dried, wherein the aqueous phase comprises 0.5 to 2 wt-% of glycerol, 2 to 8 wt-% of methanol or ethanol, 0.05 to 0.5 wt-% of undissociated soaps and 0.05 to 0.5 wt-% of FAME or FAEE, which is discharged from the separator, is thoroughly mixed with the heavy phases withdrawn from the separators of the first to penultimate reaction stages, which contain glycerol and 0.5 to 3 wt-% of FAME or FAEE, and then is supplied to a separator, in which a separation into a phase containing FAME or FAEE and a phase containing glycerol is effected.

2. The process according to claim 1, wherein the glycerol-containing phase withdrawn from the separator is thermally separated into crude glycerol and methanol or ethanol, and methanol or ethanol and the FAME or FAEE withdrawn from the separator are recirculated into the stirred-tank reactor of the first reaction stage.

3. The process according to claim 1, wherein the aqueous phase containing 0.5 to 2 wt-% of glycerol, 2 to 8 wt-% of methanol, 0.05 to 0.5 wt-% of undissociated soaps and 0.05 to 0.5 wt-% of FAME or FAEE and the phase containing glycerol with 0.5 to 3 wt-% of FAME or FAEE at a pH value of 0.5 to <6 and a temperature of 40 to 60° C. are thoroughly mixed for a period of 15 to 60 min, and the mixture is cooled to a temperature of 25 to 35° C.

4. The process according to claim 3, wherein mixing is effected at a pH value of 1 to 4 and a temperature of 40 to 50° C. for a period of 20 to 45 min.

5. The process according to claim 1, wherein the acid water washing of the crude FAME or crude FAEE is performed with a weak acid, preferably with 1 to 5% hydrochloric acid, sulfuric acid phosphoric acid or citric acid in an intensive mixer.

* * * * *